United States Patent
Thomsen

(10) Patent No.: US 7,655,260 B2
(45) Date of Patent: Feb. 2, 2010

(54) SUPPLEMENT PREPARATION

(76) Inventor: Jørn Oddershede Thomsen, Rævskærvej 21, Tornby, DK-9850 Hlrtshals (DK)

( * ) Notice: Subject to any disclaimer, the term of this patent is extended or adjusted under 35 U.S.C. 154(b) by 339 days.

(21) Appl. No.: 10/566,729

(22) PCT Filed: Aug. 2, 2004

(86) PCT No.: PCT/DK2004/000521

§ 371 (c)(1),
(2), (4) Date: Feb. 2, 2006

(87) PCT Pub. No.: WO2005/011400

PCT Pub. Date: Feb. 10, 2005

(65) Prior Publication Data

US 2006/0246147 A1  Nov. 2, 2006

(30) Foreign Application Priority Data

Aug. 5, 2003  (DK) ............................ 2003 01128

(51) Int. Cl.
*A61K 35/12* (2006.01)
*A61K 35/56* (2006.01)
*A61K 33/38* (2006.01)

(52) U.S. Cl. .................. 424/618; 424/520; 424/548

(58) Field of Classification Search ............... 424/520, 424/548, 618
See application file for complete search history.

(56) References Cited

U.S. PATENT DOCUMENTS

| 4,746,504 | A | 5/1988 | Greenman et al. |
| 6,017,901 | A | 1/2000 | Khan et al. |
| 6,528,040 | B1 * | 3/2003 | Pearson et al. ............ 424/43 |
| 6,582,713 | B2 * | 6/2003 | Newell et al. ............ 424/407 |
| 2003/0099718 | A1 | 5/2003 | Burrell et al. |

FOREIGN PATENT DOCUMENTS

| EP | 0 480 189 A | 4/1995 |
| EP | 1 308 155 A2 | 5/2003 |
| EP | 1 356 811 A1 | 10/2003 |
| FR | 2 618 677 A | 2/1989 |
| JP | 2002-145794 | 5/2002 |
| WO | WO-94/12510 | 6/1994 |
| WO | WO-96/35720 A | 11/1996 |
| WO | WO 99/13891 * | 3/1999 |

OTHER PUBLICATIONS

JT Smith, "Smith's Homeopathic Pharmacy", 1846.*
Aquaron et al., Cell Mol Biol, Jul. 2002; 48 (5): 563-569, abstract.*
Archer, Can J Cardiol, May 2008; 24 (5): 397-9.*
Harvard Health Publications, Aug. 2007.*
Database WPI, Section Ch, Week 200117, Derwent Publications Ltd., London, GB; AN 2001-161961, XP002296636 & JP 2000 309537 A (Seikagaku Kogyo Co Ltd) Nov. 7, 2000, abstract.
Database WPI, Section Ch, Week 199816, Derwent Publications Ltd., London, GB; An 1998-177283, XP002296635 & RU 2 087 148 C1 (Tretyakov V V), Aug. 20, 1997, abstract.
Database WPI, Section Ch, Week 200372, Derwent Publications Ltd., London, GB; AN 2003-762819, XP002296637, & KR 2003 018 700 A (Kim I D), Mar. 6, 2003, abstract.

* cited by examiner

*Primary Examiner*—Ruth A Davis
(74) *Attorney, Agent, or Firm*—Birch, Stewart, Kolasch & Birch, LLP

(57) ABSTRACT

Supplement preparation including (a), a first active component in form of biologically accessible silver, (b), a second active component in form of a material obtained from cartilage, and any conventional accessory agents or additives and the use of the first and the second active components with any additional active components and/or conventional accessory agent or additives for the preparation of a health-promoting supplement preparation for livestock including mink, poultry and pigs. The preparation has proved suitable for the prevention against and treatment of plasmacytosis, puppy disease, enteritis virus, three-day sickness and/or "sticky" kits in mink.

13 Claims, No Drawings

SUPPLEMENT PREPARATION

TECHNICAL FIELD

The invention relates to a prophylactic and therapeutic supplement preparation, in particular for animals.

BACKGROUND ART

For competitive reasons, modern times livestock breeding, as such breeding of furred animals and milkers, often requires large herds. This entails a high risk of infectious diseases, which may result in deaths and in serious cases necessitate the destruction of an entire herd involving heavy economic losses.

For preventing these situations, antibiotics are widely used, which should be considered alarming in the long view, as such a wide use furthers the development of antibiotic-resistant pathogenes.

In general, rational and efficient production methods are used today in modern livestock buildings, the use of which would be impossible without the use of antibiotics for both prevention and cure. This situation is for instance typical in poultry and pig production.

From an ethical assessment of the animals' welfare and suffering in connection with diseases, it is highly desirable to fulfil a primary health objective based on a significant strengthening of the animal's natural immune system as defense against various bacteria and viruses and thus allow for the removal of all antibiotics from animal production.

In mink breeding, problems with diseases such as plasmacytosis, puppy disease (caused by the distemper virus: canine distemper virus), virus enteritis, three-day sickness and sticky kits (diarrhoea condition found in minks during the suckling period and possibly caused by a too high lipid-to-protein ratio in the feed). Such diseases often result in heavy losses and increased use of antibiotics.

Silver in a biologically accessible form, such as colloidal silver, was commonly used until 1938. Since then the pharmaceutical industry has taken over the field of disease combating, and the research on colloidal silver has been shelved in competition with faster-acting and economically more lucrative drugs.

The therapeutic and prophylactic use of biologically accessible silver should be performed with the utmost caution and only in very low doses, the silver accumulating in the organism, especially in the liver, causing a weakening of the immune system. Especially at prophylactic use, where silver is administered on a regular basis, it may be difficult or practically impossible to obtain positive results without in fact deteriorating the state of health in the long view.

In the past 30 years, ox and shark cartilage has been used for the treatment of a number of diseases. It is assumed that cartilage kills cancer cells directly, stimulates the immune system and inhibits the formation of new blood vessels (angiogenesis) which the cancer cells need in order to grow uninhibitedly. A few tests are known in which cartilage has been used for the treatment of cancer in humans, but the results thereof have not been unambiguous. Shark cartilage is sold as a powder and is an excellent source of calcium, phosphor, amino acids and mucopolysaccharides.

WO 94/12510 states that in addition to the inherent nutritional benefit of shark cartilage, it is believed that two factors are also important in producing the beneficial health effects attributed to shark cartilage. One factor is the carbohydrate or mucopolysaccharide content of the shark cartilage which is believed to stimulate the immune system of the body to resist and fight disease. The second important factor is the anti angiogenic factor found in the protein portion, which can contain as many as five different active proteins.

EP-A-1 308 155 discloses an injectable solution containing a colloid of iron and shark cartilage-derived chondroitin sulphate. Such injectable solution is not suitable for a prophylactic daily use in animal breeding. Use of colloidal silver is not suggested in EP-A-1 308 155.

JP patent publication No. 2002-145794 (application No. 2001-255278) discloses an anti-arthritic or anti-rheumatic preparation containing an extract of the plant Withaia somnifera Dunal combined with an extract of cartilage, such as shark cartilage.

In the field of health food, antimony pentasulphide ($Sb_2S_5$, golden antimony sulphide) is recommended against winter coughs and bronchitis. Antimony pentasulphide is also used in combination with tin iodide, e.g. as a preparation known as "Broron-adult" or -child". The use of zinc preparations, e.g. zinc isovalerate or metallic zinc, is also recommended within the field of health food.

The recommendations in the health food field often concern very small amounts of the components in question, e.g. as a daily supplement. However, in many cases, the claimed effects are not sufficiently well documented and there has existed a widespread doubtful or skeptical attitude towards the product range of the health food market. Without considering whether the skeptical attitude is well founded or not, it may be established that these materials are not among the first ones considered by the livestock breeder for solving the above problems with infectious diseases among livestock.

It has now been found that by combining biologically accessible silver with a cartilage preparation the positive effect of silver can be enhanced to allow the use thereof in such low amounts that the unintended and detrimental accumulation of silver in the organism, e.g. in the liver, can be avoided or reduced to a harmless level.

Furthermore, it has been found that by adding very small amounts of additional selected components to such a silver/ cartilage combination, the health-promoting effect of this combination can be sustained.

It has thus been found that a preparation with a surprisingly effective prevention of diseases, including highly infectious diseases, can be formulated by means of the combination, preferably with some supplement components, which each has a proven or presumed health-promoting effect on humans. This surprising effect has already been seen in minks in areas with serious plasmacytosis problems. It seems to indicate that the said wish to completely avoid the use of antibiotics in livestock breeding can be fulfilled within a short time frame.

BRIEF DESCRIPTION OF THE INVENTION

The present invention relates to a supplement preparation including a) a first active component in form of biologically accessible silver, b) a second active component in form of a material obtained from cartilage, and any conventional accessory agents or additives.

It is assumed that an important effect of the supplement preparation is due to the fact that cartilage, such as shark cartilage, contains substances acting as catalysts on the boosting of the immune system by the biologically accessible silver such that the immune system is enhanced to a level far exceeding the effect of the individual substances. The intensifying effect has the special advantage that a positive effect can be obtained with very modest silver amounts such that the problems with silver accumulation in the liver are avoided.

Moreover, it has been found that one or more different active substances, in particular such substances recommended within the homeopathic field, directed towards diseases causing problems among the livestock in question, advantageously may be added to the supplement preparation. As a result, in addition to the effect on the immune system, which provides a general improvement of the state of health of an animal population, a noticeable combating of such specific diseases is obtained.

The supplement preparation may thus advantageously include one or more additional active components. Such additional active compounds may be selected among antimony pentasulphide, metallic tin and/or a tin salt, metallic zinc and/or a zinc salt, a sulphur containing substance and/or a iodine containing substance.

A useful sulphur containing substance is a calcium liver preparation which is commercially available as "hepar sulphuris". Examples of iodine containing substances are tin iodide, calcium iodine and tare powder.

Useful active components optionally being included in the supplement preparation are antimony pentasulphide, metallic tin and/or a tin salt, and metallic zinc and/or a zinc salt. The tin salt may be an inorganic or an organic tin salt, preferably a tin halide such as tin iodide. The zinc salt may be an inorganic or an organic zinc salt, preferably a zinc salt of an organic carboxylic acid as for instance zinc isovalerate.

Although the actual mechanism is not yet known some of the additional active components are inter alia believed to affect the liver metabolism, which further prevents silver from accumulating in the liver.

Colloidal silver is a suitable form of biologically accessible silver for use as the first component (a). A suitable cartilaginous material for use as the second active component (b) is a material, e.g. a dried powder, derived from a cartilaginous fish, preferably a shark.

The ratio between the active components (a) and (b) in the preparation according to the invention may vary greatly depending on the animal species and the ages of the animals. Usually the weight ratio a:b is between 1:100,000 and 1:10. According to a preferred embodiment the content of cartilaginous material, calculated as dry matter, is 100-12,000 parts by weight per 1 part by weight of biologically accessible silver, preferably 200-6000 parts by weight per 1 part by weight of biologically accessible silver and most preferably 300-3000 parts by weight per 1 part by weight of biologically accessible silver.

The content of the biologically accessible silver may also vary greatly depending on the animal species and the age of the animals. Usually the Ag content is between 0.1 and 100 mg per liter preparation. According to a preferred embodiment, the preparation contains 0.5-50 mg of biologically accessible silver per liter preparation, preferably 1-20 mg per liter.

The invention further relates to a use of (a), a first active component in form of biologically accessible silver, (b), a second active component in form of a material derived from cartilage, and any additional active components and/or conventional accessory agents or additives for the preparation of a health-promoting supplement preparation for livestock.

The extent of applicability of the invention appears from the following detailed description. It should, however, be understood that the detailed description and the specific examples are merely included to illustrate the preferred embodiments, and that various alterations and modifications within the scope of protection will be obvious to persons skilled in the art on the basis of the detailed description.

DETAILED DESCRIPTION OF THE INVENTION

As a base component in the preparation according to the invention biologically accessible silver is used, e.g. in form of colloid-dispersed silver in water, also denoted as colloidal silver. For the prophylactic use for minks, the silver concentration may be about 3 mg per liter, which corresponds to 3 µg/ml. In this concentration, a daily amount of about 8 ml per day may for instance be used in the feed for 100 bitches of a weight of between 1.2-1.8 kg. This corresponds to 8 ml×3 µg/ml=24 µg Ag for 100×1.5 kg body weight per day, i.e. 0.16 µg Ag per kg per day.

The silver content in the basic component of the preparation may vary, but is usually chosen from between 0.5 and 50 µg/ml. The daily dosage varies depending on the animal species in question, the animal's age, sex and general state of health, and usually between 1 ng and 1 µg Ag per kg of body weight per day.

At present, a silver concentration in the preparation for poultry is envisaged to be −5, preferably 2-3 µg/ml of silver used in a daily dosage of 0.01-0.2, preferably 0.09-0.04 µg Ag per kg body weight per day.

Correspondingly, for grown sows, a silver concentration in the preparation of 10-25, preferably 16-20 µg/ml of silver used in a daily dosage of 1 ng-0.01 µg, preferably 4-6 ng Ag per kg body weight per day is envisaged.

For mink, a silver concentration in the preparation of 0.5-10, preferably 1-6 µg/ml of silver used in a daily dosage of 0.01-0.3 µg, preferably 0.1-0.4 µg Ag per kg. body weight per day is envisaged.

According to present practice, the often-recommended dosages of colloidal silver for use in humans are of a level, which must be considered alarming due to the silver accumulation in the organism. Also as regards humans, it is expected that it is possible to obtain health-promoting effects at considerably lower and safer silver dosages by combining biologically accessible silver and a cartilaginous material. The supplement preparation according to the invention thus also has potential in relation to humans.

The second active component, derived from cartilage, may for instance be used in form of a dried and ground powder obtained as a by-product from sharks in an amount of 0.5-100 g per liter (=0.5-100 mg/ml) in the preparation, preferably 1-30 g per liter. The daily doses of the cartilaginous material typically range from 1 µg-1 mg per kg body weight, preferably from 3 µg to 0.5 mg per kg. For mink 0.2-0.8 mg/kg is typically used. For poultry 0.01-0.1 mg/kg is typically used, while the daily dosages for grown sows are envisaged to range from 1 µg to 0.01 mg per kg. It should, however, be noted that a too high dosage of cartilaginous material does not have the same serious consequence as a too high silver dosage.

In ratio to the silver amount, the cartilage powder is preferably used in an amount of 0.05-12.5 g per mg Ag, more preferably in the range from 0.1 to 7.5 g per mg Ag, and most preferably in the range from 0.5-4.0 g per mg Ag.

The combined Ag/cartilage preparation forms a sound basis for a number of supplementary active substances with health-promoting effect, in particular such substances known from the homeopathic treatment of humans. Such substances are available on the market and in the examples rendered below these have been identified on the basis of information received from the suppliers. In homeopathy, concentration specifications are used, in which for instance D6 means $1:10^{-6}$, i.e. the same as ppm. Whether such specifications denote the weight ratio (D6=mg/kg) or the weight/volume ratio (D6=1 mg/liter) is not always clear, nor is it always clear whether for instance a metallic salt is calculated on the basis of the metal ion or the entire salt molecule.

Despite these problems, the illustrative numbers stated in the present description provide the person skilled in the art with a guide as to advantageous amounts used at routine adjustments of the each of the active substances to a specific animal species or specific herds with special health problems.

It should, however, once more be emphasized that the silver as well as many of the possible supplementary additions are used in very small amounts, only about 1 ml of a product with an active substance content of from D6 to D12 ($1:10^{-12}$) being used for 1 liter of preparation, of which a daily addition of 4-8 ml to the feed for 100 animals being used or for the treatment of individual animals merely one of two drops being used.

EXAMPLES

Colloidal Silver

A colloid dispersion containing fine silver particles suspended in distilled water is prepared in a conventional electro-colloid process. By using 3 mg of silver per liter a silver dispersion of 3 μg/ml Ag is obtained.

Pau D'Arco Tea

A tea is prepared from pau d'arco—i.e. the inner bark of the tree *Tabebuia avellanedae* also known under the name of trumpet bush—by immersing a bag containing 3 g of a pau d'arco powder ("Pau d'arco Medic" supplied by Birthe Kvist Andersen of DK-9000 Aalborg) in one liter of boiling water. The mixture is left to simmer for 6 to 8 minutes whereafter the bag is removed.

Example 1

The present example described the preparation of one liter of the supplement preparation. The following constituents are used:

| | |
|---|---|
| Shark cartilage powder* | 7.5 g |
| Broron-adult** | 0.9 g |
| Zincum val D6*** | 0.4 ml |
| Hepar sulphuris D6**** | 1.0 g |
| Silver dispersion (3 μg/ml) | quantum satis 1 litre |

*"Ocean Care", which is an Australian shark cartilage powder derived from the cold-water shark (school shark; *Galeorhinus galeus*) and supplied by Natural Australian Import, DK-3550 Slangerup, Denmark.
**0.9 g of Broron-adult contains 0.9 μg active substance including antimony pentasulphide and tin iodide in lactose. Broron-adult is available from Allergica Amba, Hagemannsvej 25, DK-8600 Silkeborg.
***Zincum val D6 is a zinc preparation of zinc isovalerate; it contains 1 ppm active substance (supplier: Allergica Amba).
****Hepar sulph. D6 is a calcium sulphur liver preparation; it contains 1 ppm of active substance; available from Allergica Amba.

The remaining constituents are added to the majority of the colloid silver dispersion during stirring. Finally, the volume is adjusted to one liter with the silver dispersion.

Example 2

A supplement preparation for mink is prepared in the same manner as the preparation in example 1 based on the following constituents:

| | |
|---|---|
| Pau d'arco-tea | 15 ml |
| Shark cartilage powder | 7.5 g |
| Broron-adult | 0.9 g |
| Zincum val D6 | 0.4 ml |
| Hepar sulphuris D6 | 1.0 g |
| Calcium iodine D6* | 0.7 ml |
| Stannum met. D12** | 0.5 ml |
| *Juniperus comp.*# | 0.6 ml |
| Tricalcium citrate, monohydrate | 0.27 g |
| Tare powder## | 0.7 g |
| Silver dispersion (3 μg/ml) | quantum satis 1 litre |

*calcium-iodine-containing preparation containing 1 ppm of active substance; available from Allergica Amba.
**Tin preparation (metallic tin) containing $1:10^{-12}$ active substance; (supplier: Allergica Amba).
Combination preparation based on *Apis*, *Berberis vulgaris*, *Juniperus communis*, *Levisticum officinalis* (radix), and *Arnica* (honey bee, berberis, juniper berries, lovage root and mountain tobacco) (supplied by Allergica Amba).
Tare powder is finely pulverised tare plants (*Laminaria*). Tare are deep-sea seaweed plants (kelp) with a natural iodine content of 0.5-1%.

Example 3

A supplement preparation for poultry is prepared in the same manner as the preparation in example 1 based on the following constituents:

| | |
|---|---|
| Shark cartilage powder | 7 g |
| Broron-adult | 2.4 g |
| Zincum val D6 | 2.8 ml |
| Hepar sulphuris D6 | 3.2 g |
| Silver dispersion (2-3 μg/ml) | quantum satis 1 litre |

For grown hens having a body weight of 2-3 kg 9 ml per day is typically used for 100 hens.

Example 4

A supplement preparation for grown sows (body weight about 250 kg) is prepared in the same manner as the preparation in example 1 based on the following constituents:

| | |
|---|---|
| Shark cartilage powder | 12 g |
| Broron-adult | 1.3 g |
| Zincum met D10* | 1.4 ml |
| Hepar sulphuris D12** | 1.8 ml |
| Silver dispersion (18 μg/ml) | quantum satis 1 litre |

*Zincum met D10 is a metallic zinc preparation containing $1:10^{-10}$ of active zinc. (Supplier: Allergica Amba)
**contains $1:10^{-12}$ of active substance.

7 ml per day of the supplement preparation is typically used for 100 sows.

Example 5

A base supplement preparation for livestock is prepared in the same manner as the preparation in example 1 based on the following constituents:

| | |
|---|---|
| Shark cartilage powder | 0.5-30 g |
| Broron-adult | 0.05-20 g |

-continued

| Zincum val D6 | 0.1-10 ml |
| Hepar sulphuris D6 | 0.5-5 g |
| Tare powder | 0.3-20 g |
| Silver dispersion (1-40 µg/ml) | quantum satis 1 litre |

According to need, this base preparation may be adapted to the animal species, age and state of health by adding additional active substances.

Example 6

A base supplement preparation for livestock is prepared in the same manner as the preparation in example 1 based on the following constituents:

| Shark cartilage powder | 0.5-30 g |
| Broron-adult | 0.05-20 g |
| Zincum met D10 | 0.5-5 ml |
| Hepar sulphuris D12 | 0.5-5 ml |
| Tare powder | 0.5-10 g |
| Silver dispersion (1-40 µg/ml) | quantum satis 1 litre |

According to need, this base preparation may be adapted to the animal species, age and state of health by adding additional active substances.

Example 7

The supplement preparation made according to example 2 has been tested on a mink farm with 300 bitches and their approx. 1500 kits. From mid April the bitches received a daily dose of 8 ml per 100 bitches of the preparation as a supplement to the usual feed. From June 9, the bitches received a daily dose of 8 ml/100 bitches, while the kits received 4 ml/100 kits. On June 29, the dose was changed to 7 ml/100 animals both for bitches and for kits.

A significant improvement of the state of health was noted on the mink farm. The kits seem heavier and more vigorous than previously. There was a lower kit mortality rate, more calm bitches and only a single death during the period, which is unusual. There were no "sticky kits" even though feed was administered according to appetite after May 11. As before, a few bitches stopped lactating, i.e. premature cease of milk production. This problem thus remains unsolved, but it is most likely not linked to the immune system.

The growth of the kits was particularly good, the animals seemed to thrive optimally and their manure was of a high quality. The latter represents a measure by means of which deteriorations in the animals' state of health can be detected.

Example 8

Similar tests were carried out on three other mink farms, said tests were initiated on May 2, 2003 by administering the supplement preparation according to example 2 to 200-300 bitches per farm in a dosage of the amount as in example 6. Already in the period of June 10-15 the test was expanded to include all animals of the three farms, i.e. a total of about 7300 bitches and 37000 kits. On Jul. 12, 2003 the manager of the three mink farms reported:

a significantly lower kit mortality rate from whelping to date;
no cases of diarrhoea, mastitis or "sticky" kits, the use of antibiotics has thus not been required;
hardly any loss of breeding bitches from whelping to date;
no agitation or fights among 4-6 weeks old kits, significantly less ear sucking and neck biting;
the animals were calm with no signs of stress;
considerably increased weight at weaning;
peace and no stress after weaning, no bite injuries.
optimum use of the feed and the animals always had fine bowels movements;
good appetite without deviations after weaning;
increased growth and reduced feed consumption than normally.

Example 9

At the mink farm A the entire herd had to be destructed due to plasmacytosis. Thereafter mated beaches were bought in April 2003 from the mink farm B.

The animals at mink farm A and mink farm B were feed with the same type of feed from the same supplier during the entire period until pelting with the only difference that the animals at farm A also received the supplement preparation according to example 2 as described in example 7.

The quality of the furs obtained from almost all males were estimated at the Copenhagen Fur Center, Glostrup, Denmark and the furs were classified in five qualities and the quality index calculated. The best quality is "Saga Royal".

| | Fur type | | | |
| --- | --- | --- | --- | --- |
| | Scanglow | | Scanbrown | |
| | Mink farm A (receiving inventive supplement) | Mink farm B (without supplement) | Mink farm A (receiving inventive supplement) | Mink farm B (without supplement) |
| Saga Royal (%) | 30 | 12 | 44 | 13 |
| Saga (%) | 58 | 60 | 46 | 62 |
| A (%) | 1 | 4 | 2 | 3 |
| Quality I (%) | 11 | 23 | 7 | 22 |
| Quality II (%) | 0 | 1 | 0 | 0 |
| Quality Index | 108 | 98 | 112 | 100 |

As appears in case of Scanbrown the quality of the furs from mink farm B corresponds to the average quality (Index 100) among the about 2250 Danish minkeries supplying mink furs to Copenhagen Fur Center whereas the furs from mink farm A with index 112 are above the 95% fractile.

In most cases a mink farmer selling out a part of his animals would keep the best animals for his own breeding stock. This make the increased quality of the furs from mink farm A it even more surprising.

The above description of the invention reveals that it is obvious that it can be varied in many ways. Such variations are not to be considered a deviation from the scope of the invention, and all such modifications, which are obvious to persons skilled in the art are also to be considered comprised by the scope of the succeeding claims.

The invention claimed is:

1. Supplement preparation for therapeutic treatment of infectious diseases in animals on a daily basis by ingestion including:

a) a first active component in form of a therapeutically effective amount of biologically accessible silver in an amount of 0.5-50 mg of biologically accessible silver per liter preparation, and b) a second active component of cartilage, and c) any conventional additives, wherein the weight ratio of a:b is between 1:100,000 and 1:10.

2. Preparation according to claim 1, wherein it includes one or more additional active components.

3. Preparation according to claim 2, wherein it includes one or more additional active components selected among antimony pentasulphide, metallic tin and/or a tin salt, metallic zinc and/or a zinc salt, a sulphur containing substance and/or a iodine containing substance.

4. Preparation according to claim 3, including hepar sulphuris as a sulphur containing substance.

5. Preparation according to claim 3, including tare powder as a iodine containing substance.

6. Preparation according to claim 1, wherein the first active component (a) is a colloidal silver.

7. Preparation according to claim 1, wherein the second active component (b) is ground and/or dried cartilage.

8. Preparation according to claim 1, wherein the second active component (b) is obtained from a cartilaginous fish.

9. Preparation according to claim 1, wherein the content of cartilage, calculated as dry matter, is 100-12,000 parts by weight per 1 part by weight of biologically accessible silver.

10. A method for health-promoting treatment of infectious diseases for animals by daily treatment with a preparation comprising:

adding to animal feed or drinking water the preparation including:

(a) a first active component in form of a therapeutically effective amount of biologically accessible silver in an amount of 0.5-50 mg of biologically accessible silver per liter preparation; and (b) a second active component of cartilage, and (c) any additional active components and/or conventional accessory agents or additives, wherein the weight ratio of a:b is between 1:100,000 and 1:10; and ingesting the preparation.

11. The method according to claim 10, wherein the preparation is used for prevention and treatment of plasmacytosis, mink distemper virus, enteritis virus and/or "sticky" kits in mink.

12. The preparation according to claim 1, wherein said animal is a mink or a human.

13. The preparation according to claim 10, wherein said animal is a mink or a human.

* * * * *